(12) United States Patent
Vázquez et al.

(10) Patent No.: US 8,569,470 B2
(45) Date of Patent: Oct. 29, 2013

(54) ENGINEERED PERTACTIN VARIANTS FOR VACCINE USE

(75) Inventors: Diógenes Quintana Vázquez, Ciudad de la Habana (CU); Tamara Menendez Medina, Ciudad Habana (CU); Anabel Álvarez Acosta, Ciudad de la Habana (CU); Yoelys Cruz Leal, Ciudad de la Habana (CU); Gerardo Enrique Guillen Nieto, Ciudad de la Habana (CU)

(73) Assignee: Centro de Ingenieria Genetica y Biotecnologia, La Habana (CU)

( * ) Notice: Subject to any disclaimer, the term of this patent is extended or adjusted under 35 U.S.C. 154(b) by 307 days.

(21) Appl. No.: 12/739,658

(22) PCT Filed: Oct. 17, 2008

(86) PCT No.: PCT/CU2008/000009
§ 371 (c)(1),
(2), (4) Date: Nov. 24, 2010

(87) PCT Pub. No.: WO2009/056076
PCT Pub. Date: May 7, 2009

(65) Prior Publication Data
US 2011/0070265 A1    Mar. 24, 2011

(30) Foreign Application Priority Data
Oct. 30, 2007    (CU) .................................. 2007-0240

(51) Int. Cl.
*C07H 21/04*    (2006.01)
*A61K 39/10*    (2006.01)
(52) U.S. Cl.
USPC ...... 536/23.4; 424/254.1; 536/23.7; 435/810; 435/975

(58) Field of Classification Search
None
See application file for complete search history.

(56) References Cited

U.S. PATENT DOCUMENTS

2006/0008474 A1    1/2006    Boursaux-Eude et al.

FOREIGN PATENT DOCUMENTS

WO    01/90143 A2    11/2001
WO    02/00695 A2    1/2002

OTHER PUBLICATIONS

Houghten et al. (Vaccines, 1986, Edited by Fred Brown: Cold Spring Harbor Laboratory).*
Charles et al 1989 Proc. Natl. Acad. Sci. USA vol. 86, pp. 3554-3558.*
Fry et al 2001 Infection and immunity, vol. 69, No. 9, pp. 5520-5528.*
Charles et al Microbiology ((1994),140(12), 3301-8.*

* cited by examiner

*Primary Examiner* — Padma V Baskar
(74) *Attorney, Agent, or Firm* — Hoffmann & Baron LLP

(57) ABSTRACT

The present invention is related with the field of Biomedicine. It comprises the engineering of the Pertactin protein (Prn) and using it as part of bacterial vaccines, and more precisely, as part of acellular vaccines against *Bordetella pertusis*. The engineered Prn molecules comprise on their structure polimorfisms from different *B. pertussis* strains, and induce immune responses with protective capacity and opsonophagocytic activity when assayed as vaccines, higher than that generated by other pre-existing vaccines. The engineered Prn variants of the present invention are applicable in human and veterinary medicine.

18 Claims, 2 Drawing Sheets

SEQUENCE LISTING

<160> NUMBER OF SEQ ID NOS: 15

<210> SEQ ID NO 1
<211> LENGTH: 2613
<212> TYPE: DNA
<213> ORGANISM: Artificial Sequence
<220> FEATURE:
<223> OTHER INFORMATION: Engineered Pertactin Prn1-Prn2

<400> SEQUENCE: 1

| | | | | | |
|---|---|---|---|---|---|
| gactggaaca | accagtccat | cgtcaagacc | ggtgagcgcc | agcatggcat | ccatatccag | 60 |
| ggctccgacc | cgggcggcgt | acggaccgcc | agcggaacca | ccatcaaggt | aagcggccgt | 120 |
| caggcccagg | gcatcctgct | agaaaatccc | gcggccgagc | tgcagttccg | gaacggcagt | 180 |
| gtcacgtcgt | cgggacagtt | gtccgacgat | ggcatccggc | gctttctggg | caccgtcacc | 240 |
| gtcaaggccg | gcaagctggt | cgccgatcac | gccacgctgg | ccaacgttgg | cgacacctgg | 300 |
| gacgacgacg | gcatcgcgct | ctatgtggcc | ggcgaacagg | cccaggccag | catcgccgac | 360 |
| agcaccctgc | agggcgctgg | cggcgtgcag | atcgagcgcg | cgccaatgt | cacggtccaa | 420 |
| cgcagcgcca | tcgtcgacgg | gggcttgcat | atcggcgccc | tgcagtcatt | gcagccggaa | 480 |
| gaccttccgc | ccagccgggt | ggtgctgcgc | gacaccaacg | tgaccgccgt | gcccgccagc | 540 |
| ggcgcgcccg | cggcggtgtc | tgtgttgggg | gccagtgagc | ttacgctcga | cggcgggcac | 600 |
| atcaccggcg | gcgggcagc | ggggtggcg | gccatgcaag | gggcggtcgt | gcatctgcag | 660 |
| cgcgcgacga | tacgcgcgg | ggacgcgcct | gccggcggtg | cggttcccgg | cggtgcggtt | 720 |
| cccggtggtg | cggttcccgg | cggcttcggt | cccggcggct | tcgtccccgt | cctcgacggc | 780 |
| tggtatggcg | tggacgtatc | gggctccgtc | aaggccggca | agctggtcgc | cgatcacgcc | 840 |
| acgctggcca | acgttggcga | cacctgggac | gacgacggca | tcgcgctcta | tgtggccggc | 900 |
| gaacaggccc | aggccagcat | cgccgacagc | accctgcagg | gcgctggcgg | cgtgcagatc | 960 |
| gagcgcggcg | ccaatgtcac | ggtccaacgc | agcgccatcg | tcgacggggg | cttgcatatc | 1020 |
| ggcgccctgc | agtcattgca | gccggaagac | cttccgccca | gccgggtggt | gctgcgcgac | 1080 |
| accaacgtga | ccgccgtgcc | cgccagcggc | gcgcccgcgg | cggtgtctgt | gttgggggcc | 1140 |
| agtgagctta | cgctcgacgg | cgggcacatc | accggcgggc | gggcagcggg | ggtggcggcc | 1200 |
| atgcaagggg | cggtcgtgca | tctgcagcgc | gcgacgatac | ggcgcgggga | cgcgcctgcc | 1260 |
| ggcggtgcgg | ttcccggcgg | tgcggttccc | ggcggcttcg | gtcccggcgg | cttcgtcccc | 1320 |
| ggcggcttcg | gtcccggcgg | cttcggtccc | gtcctcgacg | gctggtatgg | cgtggacgta | 1380 |
| tcgggctcca | gcgtggagct | cgcccagtcg | atcgtcgagg | cgccggagct | gggcgccgca | 1440 |
| atccgggtgg | gccgcggcgc | cagggtgacg | gtgtcgggcg | gcagcttgtc | cgcaccgcac | 1500 |
| ggcaatgtca | tcgagaccgg | cggcgcgcgt | cgctttgcgc | tcaagccgc | gccctgtcg | 1560 |
| atcaccttgc | aggccggcgc | gcatgcccag | gggaaagcgc | tgctgtaccg | ggtcctgccg | 1620 |
| gagcccgtga | gctgacgct | gaccgggggc | gccgatgcgc | agggcgacat | cgtcgcgacg | 1680 |
| gagctgccct | ccattcccgg | cacgtcgatc | gggccgctcg | acgtggcgct | ggccagccag | 1740 |
| gcccgatgga | cgggcgctac | ccgcgcggtc | gactcgctgt | ccatcgacaa | cgccaccctgg | 1800 |
| gtcatgacgg | acaactcgaa | cgtcggtgcg | ctacggctgg | ccagcgacgg | cagcgtcgat | 1860 |
| ttccagcagc | cggccgaagc | tgggcggttc | aaggtcctga | cggtcaatac | gctggcgggt | 1920 |
| tcggggctgt | tccgcatgaa | tgtcttcgcg | gacctggggc | tgacgacaa | gctggtcgtc | 1980 |

-continued

| | |
|---|---|
| atgcaggacg ccagcggcca gcacaggctg tgggtccgca acagcggcag cgagccggcc | 2040 |
| agcgccaaca ccctgctgct ggtgcagacg ccactaggac gcgcggcgac ctttacccctt | 2100 |
| gccaacaagg acggcaaggt cgatatcggt acctatcgct atcgattggc cgccaacggc | 2160 |
| aatgggcagt ggagcctggt gggcgcgaag gcgccgccgg cgcccaagcc cgcgccgcag | 2220 |
| ccgggtcccc agccgccgca gccgccgcag ccgcagccgg aagcgccggc cgcgcaaccg | 2280 |
| ccggcgggca gggagttgtc cgccgccgcc aacgcggcgg tcaacacggg tggggtgggc | 2340 |
| ctggccagca cgctctggta cgccgaaagc aatgcgttgt ccaagcgcct gggcgagttg | 2400 |
| cgcctgaatc cggacgccgg cggcgcctgg ggccgcggct cgcgcaacg ccagcagctg | 2460 |
| gacaaccgcg ccgggcggcg cttcgaccag aaggtggccg gcttcgagct gggcgccgac | 2520 |
| cacgcggtgg cggtggccgg cggacgctgg cacctgggcg ggctggccgg ctatacgcgc | 2580 |
| ggcgaccgcg gcttcaccgg cgacggcggc ggc | 2613 |

<210> SEQ ID NO 2
<211> LENGTH: 2646
<212> TYPE: DNA
<213> ORGANISM: Artificial Sequence
<220> FEATURE:
<223> OTHER INFORMATION: Engineered Pertactin Prn1CCPrn2

<400> SEQUENCE: 2

| | |
|---|---|
| gactggaaca accagtccat cgtcaagacc ggtgagcgcc agcatggcat ccatatccag | 60 |
| ggctccgacc cgggcggcgt acggaccgcc agcggaacca ccatcaaggt aagcggccgt | 120 |
| caggcccagg gcatcctgct agaaaatccc gcggccgagc tgcagttccg gaacggcagt | 180 |
| gtcacgtcgt cgggacagtt gtccgacgat ggcatccggc gctttctggg caccgtcacc | 240 |
| gtcaaggccg gcaagctggt cgccgatcac gccacgctgg ccaacgttgg cgacacctgg | 300 |
| gacgacgacg gcatcgcgct ctatgtggcc ggcgaacagg cccaggccag catcgccgac | 360 |
| agcaccctgc agggcgctgg cggcgtgcag atcgagcgcg cgccaatgt cacggtccaa | 420 |
| cgcagcgcca tcgtcgacgg gggcttgcat atcggcgccc tgcagtcatt gcagccggaa | 480 |
| gaccttccgc ccagccgggt ggtgctgcgc gacaccaacg tgaccgccgt gcccgccagc | 540 |
| ggcgcgcccg cggcggtgtc tgtgttgggg gccagtgagc ttacgctcga cggcgggcac | 600 |
| atcaccggcg gcgggcagc ggggtggcg gccatgcaag gggcggtcgt gcatctgcag | 660 |
| cgcgcgacga tacggcgcgg ggacgcgcct gccggcggtg cggttcccgg cggtgcggtt | 720 |
| cccggtggtg cggttcccgg cggcttcggt cccggcggct cggtcccgt cctcgacggc | 780 |
| tggtatggcg tggacgtatc gggctccatc gacaacgcca cctgggtcat gacggacaac | 840 |
| gtcaaggccg gcaagctggt cgccgatcac gccacgctgg ccaacgttgg cgacacctgg | 900 |
| gacgacgacg gcatcgcgct ctatgtggcc ggcgaacagg cccaggccag catcgccgac | 960 |
| agcaccctgc agggcgctgg cggcgtgcag atcgagcgcg cgccaatgt cacggtccaa | 1020 |
| cgcagcgcca tcgtcgacgg gggcttgcat atcggcgccc tgcagtcatt gcagccggaa | 1080 |
| gaccttccgc ccagccgggt ggtgctgcgc gacaccaacg tgaccgccgt gcccgccagc | 1140 |
| ggcgcgcccg cggcggtgtc tgtgttgggg gccagtgagc ttacgctcga cggcgggcac | 1200 |
| atcaccggcg gcgggcagc ggggtggcg gccatgcaag gggcggtcgt gcatctgcag | 1260 |
| cgcgcgacga tacggcgcgg ggacgcgcct gccggcggtg cggttcccgg cggtgcggtt | 1320 |
| cccggcggct cggtcccgg cggcttcggt cccggcggct cggtcccgg cggcttcggt | 1380 |
| cccgtcctcg acggctggta tggcgtggac gtatcgggct ccagcgtgga gctcgcccag | 1440 |

-continued

| | |
|---|---|
| tcgatcgtcg aggcgccgga gctgggcgcc gcaatccggg tgggccgcgg cgccagggtg | 1500 |
| acggtgtcgg gcggcagctt gtccgcaccg cacggcaatg tcatcgagac cggcggcgcg | 1560 |
| cgtcgctttg cgcctcaagc cgcgcccctg tcgatcacct tgcaggccgg cgcgcatgcc | 1620 |
| caggggaaag cgctgctgta ccgggtcctg ccggagcccg tgaagctgac gctgaccggg | 1680 |
| ggcgccgatg cgcagggcga catcgtcgcg acggagctgc cctccattcc cggcacgtcg | 1740 |
| atcgggccgc tcgacgtggc gctggccagc caggcccgat ggacgggcgc tacccgcgcg | 1800 |
| gtcgactcgc tgtccatcga caacgccacc tgggtcatga cggacaactc gaacgtcggt | 1860 |
| gcgctacggc tggccagcga cggcagcgtc gatttccagc agccggccga agctgggcgg | 1920 |
| ttcaaggtcc tgacggtcaa tacgctggcg ggttcggggc tgttccgcat gaatgtcttc | 1980 |
| gcggacctgg ggctgagcga caagctggtc gtcatgcagg acgccagcgg ccagcacagg | 2040 |
| ctgtgggtcc gcaacagcgg cagcgagccg gccagcgcca cacccctgct gctggtgcag | 2100 |
| acgccactag gcagcgcggc gacctttacc cttgccaaca aggacggcaa ggtcgatatc | 2160 |
| ggtacctatc gctatcgatt ggccgccaac ggcaatgggc agtggagcct ggtgggcgcg | 2220 |
| aaggcgccgc cggcgcccaa gcccgcgccg cagccgggtc cccagccgcc gcagccgccg | 2280 |
| cagccgcagc cggaagcgcc ggcgccgcaa ccgccggcgg gcagggagtt gtccgccgcc | 2340 |
| gccaacgcgg cggtcaacac gggtggggtg ggcctggcca gcacgctctg gtacgccgaa | 2400 |
| agcaatgcgt tgtccaagcg cctgggcgag ttgcgcctga atccggacgc cggcggcgcc | 2460 |
| tggggccgcg gcttcgcgca acgccagcag ctggacaacc gcccggggcg gcgcttcgac | 2520 |
| cagaaggtgg ccggcttcga gctgggcgcc gaccacgcgc tggcggtggc cggcggacgc | 2580 |
| tggcacctgg gcgggctggc cggctatacg cgcggcgacc gcggcttcac cggcgacggc | 2640 |
| ggcggc | 2646 |

<210> SEQ ID NO 3
<211> LENGTH: 2679
<212> TYPE: DNA
<213> ORGANISM: Artificial Sequence
<220> FEATURE:
<223> OTHER INFORMATION: Engineered Pertactin Prn1CLPrn2

<400> SEQUENCE: 3
gactggaaca accagtccat cgtcaagacc ggtgagcgcc agcatggcat ccatatccag 60
ggctccgacc cgggcggcgt acggaccgcc agcggaacca ccatcaaggt aagcggccgt 120
caggcccagg gcatcctgct agaaaatccc gcggccgagc tgcagttccg gaacggcagt 180
gtcacgtcgt cgggacagtt gtccgacgat ggcatccggc gctttctggg caccgtcacc 240
gtcaaggccg gcaagctggt cgccgatcac gccacgctgg ccaacgttgg cgacacctgg 300
gacgacgacg gcatcgcgct ctatgtggcc ggcgaacagg cccaggccag catcgccgac 360
agcaccctgc agggcgctgg cggcgtgcag atcgagcgcg gcgccaatgt cacggtccaa 420
cgcagcgcca tcgtcgacgg gggcttgcat atcggcgccc tgcagtcatt gcagccggaa 480
gaccttccgc ccagccgggt ggtgctgcgc gacaccaacg tgaccgccgt gcccgccagc 540
ggcgcgcccg cggcggtgtc tgtgttgggg gccagtgagc ttacgctcga cggcgggcac 600
atcaccggcg ggcgggcagc gggggtggcg gccatgcaag ggcggtcgt gcatctgcag 660 cgcgcgacga tacggcgcgg ggacgcgcct gccggcggtg cggttcccgg cggtgcggtt 720
cccggtggtg cggttcccgg cggcttcggt cccggcggct tcggtcccgt cctcgacggc 780
tggtatggcg tggacgtatc gggctccatc gacaacgcca cctgggtcat gacggacaac 840

-continued

| | |
|---|---|
| atcgacaacg ccacctgggt catgacggac aacgtcaagg ccggcaagct ggtcgccgat | 900 |
| cacgccacgc tggccaacgt tggcgacacc tgggacgacg acggcatcgc gctctatgtg | 960 |
| gccggcgaac aggcccaggc cagcatcgcc gacagcaccc tgcagggcgc tggcggcgtg | 1020 |
| cagatcgagc gcggcgccaa tgtcacggtc aacgcagcg ccatcgtcga cgggggcttg | 1080 |
| catatcggcg ccctgcagtc attgcagccg aagaccttc cgcccagccg ggtggtgctg | 1140 |
| cgcgacacca acgtgaccgc cgtgcccgcc agcggcgcgc ccgcggcggt gtctgtgttg | 1200 |
| ggggccagtg agcttacgct cgacggcggg cacatcaccg gcgggcgggc agcggggtg | 1260 |
| gcggccatgc aagggcggt cgtgcatctg cagcgcgcga cgatacgcg cggggacgcg | 1320 |
| cctgccggcg gtgcggttcc cggcggtgcg gttcccggcg gcttcggtcc cggcggcttc | 1380 |
| ggtcccggcg gcttcggtcc cggcggcttc ggtcccgtcc tcgacggctg gtatggcgtg | 1440 |
| gacgtatcgg gctccagcgt ggagctcgcc cagtcgatcg tcgaggcgcc ggagctgggc | 1500 |
| gccgcaatcc gggtgggccg cggcgccagg gtgacggtgt cgggcggcag cttgtccgca | 1560 |
| ccgcacggca atgtcatcga gaccggcggc gcgcgtcgct ttgcgcctca agccgcgccc | 1620 |
| ctgtcgatca ccttgcaggc cggcgcgcat gcccagggga aagcgctgct gtaccgggtc | 1680 |
| ctgccggagc ccgtgaagct gacgctgacc gggggcgccg atgcgcaggg cgacatcgtc | 1740 |
| gcgacggagc tgccctccat tcccggcacg tcgatcgggc cgctcgacgt ggcgctggcc | 1800 |
| agccaggccc gatgacgggg cgctacccgc gcggtcgact cgctgtccat cgacaacgcc | 1860 |
| acctgggtca tgacggacaa ctcgaacgtc ggtgcgctac ggctggccag cgacggcagc | 1920 |
| gtcgatttcc agcagccggc cgaagctggg cggttcaagg tcctgacggt caatacgctg | 1980 |
| gcgggttcgg ggctgttccg catgaatgtc ttcgcggacc tggggctgag cgacaagctg | 2040 |
| gtcgtcatgc aggacgccag cggccagcac aggctgtggg tccgcaacag cggcagcgag | 2100 |
| ccggccagcg ccaacaccct gctgctggtg cagacgccac taggcagcgc ggcgaccttt | 2160 |
| accccttgcca acaaggacgg caaggtcgat atcggtacct atcgctatcg attggccgcc | 2220 |
| aacggcaatg ggcagtggag cctggtgggc gcgaaggcgc cgccggcgcc caagcccgcg | 2280 |
| ccgcagccgg gtccccagcc gccgcagccg ccgcagccgc agccggaagc gccggcgccg | 2340 |
| caaccgccgg cgggcaggga gttgtccgcc gccgccaacg cggcggtcaa cacgggtggg | 2400 |
| gtgggcctgg ccagcacgct ctggtacgcc gaaagcaatg cgttgtccaa cgcctgggc | 2460 |
| gagttgcgcc tgaatccgga cgccggcggc gcctggggcc gcggcttcgc gcaacgccag | 2520 |
| cagctggaca accgcgccgg gcggcgcttc gaccagaagg tggccggctt cgagctgggc | 2580 |
| gccgaccacg cggtggcggt ggccggcgga cgctggcacc tgggcgggct ggccggctat | 2640 |
| acgcgcggcg accgcggctt caccggcgac ggcggcggc | 2679 |

<210> SEQ ID NO 4
<211> LENGTH: 2613
<212> TYPE: DNA
<213> ORGANISM: Artificial Sequence
<220> FEATURE:
<223> OTHER INFORMATION: Engineered Pertactin Prn2-Prn1

<400> SEQUENCE: 4

| | |
|---|---|
| gactggaaca accagtccat cgtcaagacc ggtgagcgcc agcatggcat ccatatccag | 60 |
| ggctccgacc cggcggcgt acggaccgcc agcggaacca ccatcaaggt aagcggccgt | 120 |
| caggcccagg gcatcctgct agaaaatccc gcggccgagc tgcagttccg gaacggcagt | 180 |
| gtcacgtcgt cgggacagtt gtccgacgat ggcatccggc gctttctggg caccgtcacc | 240 |

```
gtcaaggccg gcaagctggt cgccgatcac gccacgctgg ccaacgttgg cgacacctgg      300
gacgacgacg gcatcgcgct ctatgtggcc ggcgaacagg cccaggccag catcgccgac      360
agcaccctgc agggcgctgg cggcgtgcag atcgagcgcg gcgccaatgt cacggtccaa      420
cgcagcgcca tcgtcgacgg gggcttgcat atcggcgccc tgcagtcatt gcagccggaa      480
gaccttccgc ccagccgggt ggtgctgcgc gacaccaacg tgaccgccgt gcccgccagc      540
ggcgcgcccg cggcggtgtc tgtgttgggg ccagtgagc ttacgctcga cggcgggcac       600
atcaccggcg ggcgggcagc gggggtggcg gccatgcaag gggcggtcgt gcatctgcag      660
cgcgcgacga tacggcgcgg ggacgcgcct gccggcggtg cggttcccgg cggtgcggtt      720
cccggcggct tcggtcccgg cggcttcggt cccggcggct tcggtcccgg cggcttcggt      780
cccgtcctcg acgctggta tggcgtggac gtatcgggct ccgtcaaggc cggcaagctg       840
gtcgccgatc acgccacgct ggccaacgtt ggcgacacct gggacgacga cggcatcgcg      900
ctctatgtgg ccgcgaaca ggcccaggcc agcatcgccg acagcaccct gcagggcgct       960
ggcggcgtgc agatcgagcg cggcgccaat gtcacggtcc aacgcagcgc catcgtcgac     1020
gggggcttgc atatcggcgc cctgcagtca ttgcagccgg aagaccttcc gcccagccgg     1080
gtggtgctgc gcgacaccaa cgtgaccgcc gtgcccgcca gcgcgcgcc cgcggcggtg      1140 tctgtgttgg gggccagtga gcttacgctc gacggcgggc acatcaccgg cgggcgggca     1200
gcgggggtgg cggccatgca aggggcggtc gtgcatctgc agcgcgcgac gatacggcgc     1260
ggggacgcgc ctgccggcgg tgcggttccc ggcggtgcgg ttcccggtgg tgcggttccc     1320
ggcggcttcg gtcccggcgg cttcggtccc gtcctcgacg ctggtatgg cgtggacgta      1380 tcgggctcca gcgtggagct cgcccagtcg atcgtcgagg cgccggagct gggcgccgca     1440
atccgggtgg gccgcggcgc cagggtgacg gtgtcgggcg gcagcttgtc cgcaccgcac     1500
ggcaatgtca tcgagaccgg cggcgcgcgt cgctttgcgc ctcaagccgc gcccctgtcg     1560
atcaccttgc aggccggcgc gcatgcccag gggaaagcgc tgctgtaccg ggtcctgccg     1620
gagcccgtga agctgacgct gaccgggggc gccgatgcgc agggcgacat cgtcgcgacg     1680
gagctgccct ccattcccgg cacgtcgatc gggccgctcg acgtggcgct ggccagccag     1740
gcccgatgga cgggcgctac ccgcgcggtc gactcgctgt ccatcgacaa cgccacctgg     1800
gtcatgacgg acaactcgaa cgtcggtgcg ctacggctgg ccagcgacgg cagcgtcgat     1860
ttccagcagc cggccgaagc tgggcggttc aaggtcctga cggtcaatac gctggcgggt     1920
tcggggctgt ccgcatgaa tgtcttcgcg gacctgggc tgagcgacaa gctggtcgtc       1980
atgcaggacg ccagcggcca gcacaggctg tgggtccgca acagcggcag cgagccggcc     2040
agcgccaaca ccctgctgct ggtgcagacg ccactaggca gcgcggcgac ctttaccctt     2100
gccaacaagg acggcaaggt cgatatcggt acctatcgct atcgattggc cgccaacggc     2160
aatgggcagt ggagcctggt gggcgcgaag gcgccgccgg cgcccaagcc cgcgccgcag     2220
ccgggtcccc agccgccgca gccgccgcag ccgcagccgg aagcgccggc gccgcaaccg     2280
ccggcgggca gggagttgtc cgccgccgcc aacgcggcgg tcaacacggg tggggtgggc     2340
ctggccagca cgctctggta cgccgaaagc aatgcgttgt ccaagcgcct gggcgagttg     2400
cgcctgaatc cggacgccgg cggcgcctgg ggccgcggct tcgcgcaacg ccagcagctg     2460
gacaaccgcg ccgggcggcg cttcgaccag aaggtggccg gcttcgagct gggcgccgac     2520
cacgcggtgg cggtggccgg cggacgctgg cacctgggcg gctggccgg ctatacgcgc      2580 ggcgaccgcg gcttcaccgg cgacggcggc ggc                                  2613
```

<210> SEQ ID NO 5
<211> LENGTH: 2646
<212> TYPE: DNA
<213> ORGANISM: Artificial Sequence
<220> FEATURE:
<223> OTHER INFORMATION: Engineered Pertactin Prn2CCPrn1

<400> SEQUENCE: 5

```
gactggaaca accagtccat cgtcaagacc ggtgagcgcc agcatggcat ccatatccag     60
ggctccgacc cgggcggcgt acggaccgcc agcggaacca ccatcaaggt aagcggccgt    120
caggcccagg gcatcctgct agaaaatccc gcggccgagc tgcagttccg gaacggcagt    180
gtcacgtcgt cgggacagtt gtccgacgat ggcatccggc gctttctggg caccgtcacc    240
gtcaaggccg gcaagctggt cgccgatcac gccacgctgg ccaacgttgg cgacacctgg    300
gacgacgacg gcatcgcgct ctatgtggcc ggcgaacagg cccaggccag catcgccgac    360
agcaccctgc agggcgctgg cggcgtgcag atcgagcgcg gcgccaatgt cacggtccaa    420
cgcagcgcca tcgtcgacgg gggcttgcat atcggcgccc tgcagtcatt gcagccggaa    480
gaccttccgc ccagccgggt ggtgctgcgc gacaccaacg tgaccgccgt gcccgccagc    540
ggcgcgcccg cggcggtgtc tgtgttgggg gccagtgagc ttacgctcga cggcgggcac    600
atcaccggcg ggcgggcagc gggggtggcg gccatgcaag ggcggtcgt gcatctgcag    660 cgcgcgacga tacggcgcgg ggacgcgcct gccggcggtg cggttcccgg cggtgcggtt    720
cccggcggct tcggtcccgg cggcttcggt cccggcggct tcggtcccgg cggcttcggt    780
cccgtcctcg acggctggta tggcgtggac gtatcgggct ccatcgacaa cgccacctgg    840
gtcatgacgg acaacgtcaa ggccggcaag ctggtcgccg atcacgccac gctggccaac    900
gttggcgaca cctgggacga cgacggcatc gcgctctatg tggccggcga acaggcccag    960
gccagcatcg ccgacagcac cctgcagggc gctggcggcg tgcagatcga gcgcggcgcc   1020
aatgtcacgg tccaacgcag cgccatcgtc gacgggggct tgcatatcgg cgccctgcag   1080
tcattgcagc cggaagacct tccgcccagc cgggtggtgc tgcgcgacac caacgtgacc   1140
gccgtgcccg ccagcggcgc gcccgcggcg gtgtctgtgt tgggggccag tgagcttacg   1200
ctcgacggcg ggcacatcac cggcgggcgg gcagcggggg tggcggccat gcaaggggcg   1260
gtcgtgcatc tgcagcgcgc gacgatacgg cgcggggacg cgcctgccgg cggtgcggtt   1320
cccggcggtg cggttcccgg tggtgcggtt cccggcggct tcggtcccgg cggcttcggt   1380
cccgtcctcg acggctggta tggcgtggac gtatcgggct ccagcgtgga gctcgcccag   1440
tcgatcgtcg aggcgccgga gctgggcgcc gcaatccggg tgggccgcgg cgccagggtg   1500
acggtgtcgg gcggcagctt gtccgcaccg cacggcaatg tcatcgagac cggcggcgcg   1560
cgtcgctttg cgcctcaagc cgcgcccctg tcgatcacct tgcaggccgg cgcgcatgcc   1620
caggggaaag cgctgctgta ccgggtcctg ccggagcccg tgaagctgac gctgaccggg   1680
ggcgccgatg cgcagggcga catcgtcgcg acggagctgc cctccattcc cggcacgtcg   1740
atcgggccgc tcgacgtggc gctggccagc caggcccgat ggacgggcgc tacccgcgcg   1800
gtcgactcgc tgtccatcga caacgccacc tgggtcatga cggacaactc gaacgtcggt   1860
gcgctacggc tggccagcga cggcagcgtc gatttccagc agccggccga agctgggcgg   1920
ttcaaggtcc tgacggtcaa tacgctggcg ggttcggggc tgttccgcat gaatgtcttc   1980
gcggacctgg ggctgagcga caagctggtc gtcatgcagg acgccagcgg ccagcacagg   2040
ctgtgggtcc gcaacagcgg cagcgagccg gccagcgcca acaccctgct gctggtgcag   2100
```

-continued

| | |
|---|---|
| acgccactag gcagcgcggc gacctttacc cttgccaaca aggacggcaa ggtcgatatc | 2160 |
| ggtacctatc gctatcgatt ggccgccaac ggcaatgggc agtggagcct ggtgggcgcg | 2220 |
| aaggcgccgc cggcgcccaa gcccgcgccg cagccgggtc cccagccgcc gcagccgccg | 2280 |
| cagccgcagc cggaagcgcc ggcgccgcaa ccgccggcgg gcagggagtt gtccgccgcc | 2340 |
| gccaacgcgg cggtcaacac gggtgggtg ggcctggcca gcacgctctg gtacgccgaa | 2400 |
| agcaatgcgt tgtccaagcg cctgggcgag ttgcgcctga atccgacgc cggcggcgcc | 2460 |
| tggggccgcg gcttcgcgca acgccagcag ctggacaacc gcgccgggcg gcgcttcgac | 2520 |
| cagaaggtgg ccggcttcga gctgggcgcc gaccacgcgg tggcggtggc cggcggacgc | 2580 |
| tggcacctgg gcgggctggc cggctatacg cgcggcgacc gcggcttcac cggcgacggc | 2640 |
| ggcggc | 2646 |

<210> SEQ ID NO 6
<211> LENGTH: 2679
<212> TYPE: DNA
<213> ORGANISM: Artificial Sequence
<220> FEATURE:
<223> OTHER INFORMATION: Engineered Pertactin Prn2CLPrn1

<400> SEQUENCE: 6

| | |
|---|---|
| gactggaaca accagtccat cgtcaagacc ggtgagcgcc agcatggcat ccatatccag | 60 |
| ggctccgacc cgggcggcgt acggaccgcc agcggaacca ccatcaaggt aagcggccgt | 120 |
| caggcccagg gcatcctgct agaaaatccc gcggccgagc tgcagttccg gaacggcagt | 180 |
| gtcacgtcgt cgggacagtt gtccgacgat ggcatccggc gctttctggg caccgtcacc | 240 |
| gtcaaggccg gcaagctggt cgccgatcac gccacgctgg ccaacgttgg cgacaccctgg | 300 |
| gacgacgacg gcatcgcgct ctatgtggcc ggcgaacagg cccaggccag catcgccgac | 360 |
| agcaccctgc agggcgctgg cggcgtgcag atcgagcgcg cgccaatgt cacggtccaa | 420 |
| cgcagcgcca tcgtcgacgg gggcttgcat atcggcgccc tgcagtcatt gcagccggaa | 480 |
| gaccttccgc ccagccgggt ggtgctgcgc gacaccaacg tgaccgccgt gcccgccagc | 540 |
| ggcgcgcccg cggcggtgtc tgtgttgggg gccagtgagc ttacgctcga cggcgggcac | 600 |
| atcaccggcg ggcgggcagc gggggtggcg gccatgcaag gggcggtcgt gcatctgcag | 660 |
| cgcgcgacga tacggcgcgg ggacgcgcct gccggcggtg cggttcccgg cggtgcggtt | 720 |
| cccggcggct tcggtcccgg cggcttcggt cccggcggct tcggtcccgg cggcttcggt | 780 |
| cccgtcctcg acggctggta tggcgtgac gtatcgggct ccatcgacaa cgccaccctgg | 840 |
| gtcatgacgg acaacatcga caacgccacc tgggtcatga cggacaacgt caaggccggc | 900 |
| aagctggtcg ccgatcacgc cacgctgcc aacgttggcg acacctggga cgacgacggc | 960 |
| atcgcgctct atgtggccgg cgaacaggcc caggccagca tcgccgacag caccctgcag | 1020 |
| ggcgctggcg gcgtgcagat cgagcgcggc gccaatgtca cggtccaacg cagcgccatc | 1080 |
| gtcgacgggg gcttgcatat cggcgccctg cagtcattgc agccggaaga ccttccgccc | 1140 |
| agccgggtgt gctgcgcga caccaacgtg accgccgtgc cgccagcgg cgcgcccgcg | 1200 |
| gcggtgtctg tgttgggggc cagtgagctt acgctcgacg gcgggcacat caccggcggg | 1260 |
| cgggcagcgg gggtggcggc catgcaaggg gcggtcgtg atctgcagcg cgcgacgata | 1320 |
| cggcgcgggg acgcgcctgc cggcggtgcg gttcccggcg gtgcggttcc cggtggtgcg | 1380 |
| gttcccggcg gcttcggtcc cggcggcttc ggtcccgtcc tcgacggctg gtatggcgtg | 1440 |
| gacgtatcgg gctccagcgt ggagctcgcc cagtcgatcg tcgaggcgcc ggagctgggc | 1500 |

```
gccgcaatcc gggtgggccg cggcgccagg gtgacggtgt cgggcggcag cttgtccgca    1560
ccgcacggca atgtcatcga gaccggcggc gcgcgtcgct ttgcgcctca agccgcgccc    1620
ctgtcgatca ccttgcaggc cggcgcgcat gcccagggga aagcgctgct gtaccgggtc    1680
ctgccggagc ccgtgaagct gacgctgacc ggggggcgccg atgcgcaggg cgacatcgtc    1740
gcgacggagc tgccctccat tcccggcacg tcgatcgggc cgctcgacgt ggcgctggcc    1800
agccaggccc gatggacggg cgctacccgc gcggtcgact cgctgtccat cgacaacgcc    1860
acctgggtca tgacggacaa ctcgaacgtc ggtgcgctac ggctggccag cgacggcagc    1920
gtcgatttcc agcagccggc cgaagctggg cggttcaagg tcctgacggt caatacgctg    1980
gcgggttcgg ggctgttccg catgaatgtc ttcgcggacc tggggctgag cgacaagctg    2040
gtcgtcatgc aggacgccag cggccagcac aggctgtggg tccgcaacag cggcagcgag    2100
ccggccagcg ccaacaccct gctgctggtg cagacgccac taggcagcgc ggcgaccttt    2160
acccttgcca caaggacgg caaggtcgat atcggtacct atcgctatcg attggccgcc    2220
aacggcaatg ggcagtggag cctggtgggc gcgaaggcgc cgccggcgcc caagcccgcg    2280
ccgcagccgg gtccccagcc gccgcagccg ccgcagccgc agccgaagc gccggcgccg    2340 caaccgccgg cgggcaggga gttgtccgcc gccgccaacg cggcggtcaa cacgggtggg    2400
gtgggcctgg ccagcacgct ctggtacgcc gaaagcaatg cgttgtccaa gcgcctgggc    2460
gagttgcgcc tgaatccgga cgccggcggc gcctggggcc gcggcttcgc gcaacgccag    2520
cagctggaca accgcgccgg gcggcgcttc gaccagaagg tggccggctt cgagctgggc    2580
gccgaccacg cggtggcggt ggccggcgga cgctggcacc tgggcgggct ggccggctat    2640
acgcgcggcg accgcggctt caccggcgac ggcggcggc                           2679
```

```
<210> SEQ ID NO 7
<211> LENGTH: 5
<212> TYPE: PRT
<213> ORGANISM: Artificial Sequence
<220> FEATURE:
<223> OTHER INFORMATION: Repetitive Sequence found in Prn Protein of
      B. pertussis
<220> FEATURE:
<221> NAME/KEY: misc_feature
<222> LOCATION: (3)..(4)
<223> OTHER INFORMATION: Xaa can be any naturally occurring amino acid

<400> SEQUENCE: 7

Gly Gly Xaa Xaa Pro
1               5

<210> SEQ ID NO 8
<211> LENGTH: 11
<212> TYPE: PRT
<213> ORGANISM: Artificial Sequence
<220> FEATURE:
<223> OTHER INFORMATION: Linker

<400> SEQUENCE: 8

Ile Asp Asn Ala Thr Trp Val Met Thr Asp Asn
1               5                   10

<210> SEQ ID NO 9
<211> LENGTH: 22
<212> TYPE: PRT
<213> ORGANISM: Artificial Sequence
<220> FEATURE:
<223> OTHER INFORMATION: Linker

<400> SEQUENCE: 9
```

Ile Asp Asn Ala Thr Trp Val Met Thr Asp Asn Ile Asp Asn Ala Thr
1               5                   10                  15

Trp Val Met Thr Asp Asn
            20

<210> SEQ ID NO 10
<211> LENGTH: 30
<212> TYPE: PRT
<213> ORGANISM: Artificial Sequence
<220> FEATURE:
<223> OTHER INFORMATION: Primer

<400> SEQUENCE: 10

Ala Gly Cys Gly Thr Gly Gly Ala Gly Cys Thr Cys Gly Cys Cys
1               5                   10                  15

Ala Gly Thr Cys Gly Ala Thr Cys Gly Thr Cys Gly Ala Gly
            20                  25                  30

<210> SEQ ID NO 11
<211> LENGTH: 30
<212> TYPE: PRT
<213> ORGANISM: Artificial Sequence
<220> FEATURE:
<223> OTHER INFORMATION: Primer

<400> SEQUENCE: 11

Gly Gly Ala Gly Cys Cys Cys Gly Ala Thr Ala Cys Gly Thr Cys Cys
1               5                   10                  15

Ala Cys Gly Cys Cys Ala Thr Ala Cys Cys Ala Gly Cys Cys
            20                  25                  30

<210> SEQ ID NO 12
<211> LENGTH: 23
<212> TYPE: PRT
<213> ORGANISM: Artificial Sequence
<220> FEATURE:
<223> OTHER INFORMATION: Primer

<400> SEQUENCE: 12

Gly Thr Cys Ala Ala Gly Gly Cys Cys Gly Gly Cys Ala Ala Gly Cys
1               5                   10                  15

Thr Gly Gly Thr Cys Gly Cys
            20

<210> SEQ ID NO 13
<211> LENGTH: 23
<212> TYPE: PRT
<213> ORGANISM: Artificial Sequence
<220> FEATURE:
<223> OTHER INFORMATION: Primer

<400> SEQUENCE: 13

Gly Gly Ala Gly Cys Cys Cys Gly Ala Thr Ala Cys Gly Thr Cys Cys
1               5                   10                  15

Ala Cys Gly Cys Cys Ala Thr
            20

<210> SEQ ID NO 14
<211> LENGTH: 56
<212> TYPE: PRT
<213> ORGANISM: Artificial Sequence
<220> FEATURE:
<223> OTHER INFORMATION: Primer

<400> SEQUENCE: 14

```
Ala Thr Cys Gly Ala Cys Ala Ala Cys Gly Cys Cys Ala Cys Cys Thr
1               5                   10                  15

Gly Gly Gly Thr Cys Ala Thr Gly Ala Cys Gly Gly Ala Cys Ala Ala
                20                  25                  30

Cys Gly Thr Cys Ala Ala Gly Gly Cys Cys Gly Gly Cys Ala Ala Gly
            35                  40                  45

Cys Thr Gly Gly Thr Cys Gly Cys
        50                  55

<210> SEQ ID NO 15
<211> LENGTH: 84
<212> TYPE: PRT
<213> ORGANISM: Artificial Sequence
<220> FEATURE:
<223> OTHER INFORMATION: Primer

<400> SEQUENCE: 15

Ala Thr Cys Gly Ala Cys Ala Ala Cys Gly Cys Cys Ala Cys Cys Thr
1               5                   10                  15

Gly Gly Gly Thr Cys Ala Thr Gly Ala Cys Gly Gly Ala Cys Ala Ala
                20                  25                  30

Cys Ala Thr Cys Gly Ala Cys Ala Ala Cys Gly Cys Cys Ala Cys Cys
            35                  40                  45

Thr Gly Gly Gly Thr Cys Ala Thr Gly Ala Cys Gly Gly Ala Cys Ala
        50                  55                  60

Ala Cys Gly Thr Cys Ala Ala Gly Gly Cys Cys Gly Gly Cys Ala Ala
65                  70                  75                  80

Gly Cys Thr Gly
```

ENGINEERED PERTACTIN VARIANTS FOR VACCINE USE

CLAIM OF PRIORITY

This application is the U.S. National Phase of, and Applicants claim priority from, International Application Number PCT/CU2008/000009 filed 17 Oct. 2008 and Cuban Patent Application No. 2007-0240 filed 30 Oct. 2007, which are incorporated herein by reference.

INCORPORATION OF SEQUENCE LISTING

Incorporated herein by reference in its entirety is the Sequence Listing for the above-identified application. The Sequence Listing is disclosed on a computer-readable ASCII text file titled "Sub_Sequence_976-72PCT_US.txt" having a size of 26 KB, created on Jun. 29, 2012.

TECHNICAL FIELD

The present invention is related with the field of Biomedicine. It comprises the engineering of the Pertactin protein (Prn) and using it as part of bacterial vaccines, and more precisely, as part of acellular vaccines against *Bordetella pertusis*. The engineered Prn molecules comprise on their structure polimorfisms from different *B. pertussis* strains, and induce immune responses with increased protective capacity and opsonophagocytic activity when assayed as vaccines, higher than that generated by other pre-existing vaccines.

BACKGROUND OF THE INVENTION

Whooping Cough or *Pertussis* is an acute, highly infectious respiratory disease caused by the *Bordetella pertussis* bacterium, a microorrganism formerly isolated by Bordet and Gengou in 1906 [Bordet, J. and O. Gengou. Ann Inst Pasteur (Paris), 1906. 20: p. 731-41]. Recently, the annual morbidity of infections throughout the world was estimated in 48.5 millions. The disease is particularly severe in children with less than six months of age, with 90% of the casualties being associated to this ethareal group (300,000-400,000) [Crowcroft, N. S., et al. Lancet Infect Dis, 2003. 3(7): p. 413-8].

Several vaccines are available against *B. pertussis*, distributed in two main groups according to their type: cellular vaccines, and, more recently, acellular vaccines. Vaccination has dramatically decreased the incidence of the disease, moving it from children towards teenager and adult populations. Several studies have shown teenagers as the major reservoir for *B. pertussis* and the main source for spreading of this disease among partially protected children. Therefore, whooping cough remains as an unsolved health problem, demanding the development of new vaccines for a better control of the epidemics and re-emergent outbreaks, and possibly to eradicate this disease in endemic regions [Cherry, J. D. Pediatrics, 2005. 115(5): p. 1422-7; Singh, M. and K. Lingappan, Chest, 2006. 130(5): p. 1547-53]. The *Bordetella* genera includes nine species, four of them being associated to infections in mammals (*B. holmesii, B. bronchiseptica, B. parapertussis* and *B. pertussis*), the last two being responsible for infections in humans [Mattoo, S., et al. Front Biosci, 2001. 6: p. E168-86]. Most of their virulence factors are regulated at transcriptional level by a two-components system denominated BvgA/S (*Bordetella* virulence genes Activator/Sensor) [Stibitz, S., et al. Nature, 1989. 338(6212): p. 266-9]. Among them, the most relevant factors are the *Pertussis* toxins (PT), the tracheal colonization factor, adenylate cyclase; and adhesins filamentous Phytohemagglutinin (PHA), Fimbriae (Fim) and Pertactin (Prn), the latter being the focus of the present invention.

Prn is an outer membrane protein belonging to the family of type V autotransporter proteins. It is characterized by catalyzing its own transportation through the bacterial outer membrane [Henderson, I.R. Trends Microbiol, 2000. 8(12): p. 534-5]. The mature Prn is a protein of 68 kDa in *B. bronchiseptica* [Henderson, I.R. Infect Immun, 2001. 69(3): p. 1231-43.], 69 kDa in *B. pertussis* [Charles, I. G., et al. Proc Natl Acad Sci USA, 1989. 86(10): p. 3554-8] and 70 kDa in *B. parapertussis* [Li, L. J., et al al. Mol Microbiol, 1991. 5(2): p. 409-17], respectively. Its structure consists on 16 paralel strands forming a β helix and a transversal section in V form [Emsley, P., et al. Nature, 1996. 381(6577): p. 90-2.]. Numerous loops protrude from this helicoidal core. One of them is the Arg-Gly-Asp triplete (RGD), a motif associated to tissue adherence [Leininger, E., et al. Infect Immun, 1992. 60(6): p. 2380-5; Emsley, P., et al. Nature, 1996. 381(6577): p. 90-2]. The presence of this motif and numerous proline-rich regions are related to Prn functions during adhesion. Experiments have shown that the Prn can mediate adhesion to cells of the respiratory epithelium [Everest, P., et al. Microbiology, 1996. 142 (Pt 11): p. 3261-8]. Nevertheless, assays on the inhibition by human sera of *B. pertussis* adhesion to A549 cultured cells (alveolar human epithelium) did not evidence Prn as a crucial element during that process under the tested conditions [Rodriguez, M. E., et al. FEMS Immunol Med Microbiol, 2006. 46(1): p. 39-47].

The Prn protein is part of acellular vaccines composed of three or more components. Acellualr vaccines can be composed of: 1) one component of PT, 2) two components: PT and PHA, 3) three components: PT, PHA and Prn, and 4) five components, including the three components previously mentioned and also the Fimbriae 2 (Fim2) and Fimbriae 3 (Fim3) proteins. In humans, the levels of the anti-Prn, anti-Fim2 and anti-PT antibodies correlate with protection levels against the disease [Cherry, J. D., et al. Vaccine, 1998. 16(20): p. 1901-6; Storsaeter, J., et al. Vaccine, 2003. 21(25-26): p. 3542-9].

The active immunization with Prn of *B. pertussis* and *B. bronchiseptica* induces a specific antibody response against Prn, conferring protection in different animal models [Charles, I. G., et al. Eur J Immunol, 1991. 21(5): p. 1147-53; Roberts, M., et al. Vaccine, 1992. 10(1): p. 43-8]. Similarly, the passive administration of anti-Prn monoclonal antibodies (MAbs) protected mice in the model of respiratory challenge [King, A. J., et al. Microbiology, 2001. 147(Pt 11): p. 2885-95]. Protection levels in mice subjected to the intranasal challenge assay (INCA) were increased by adding Prn to vaccines containing PT and PHA [Guiso, N., et al. Vaccine, 1999. 17(19): p. 2366-76]. It has been recently shown that Prn is the only component of acellular vaccines which generates an antibody response of such a level that correlates to the opsonophagocytic activity [Hellwig, S. M., et al. J Infect Dis, 2003. 188(5): p. 738-42]. In spite of efficacious vaccines and the well established vaccination programs available, whooping cough is still endemic in regions of America, Europe and Asia, being considered as a re-emergent disease [Raguckas, S. E., et al. Pharmacotherapy, 2007. 27(1): p. 41-52]. One of the hypotheses trying to explain this phenomenon is based on the loss of efficacy, due to appearance of resistant strains [Mooi, F. R et al. Emerg Infect Dis, 2001. 7(3 Suppl): p. 526-8]. Prn is one of the most polymorphic proteins in *B. pertussis*. It contains two variable regions designated as region 1 (R1) and 2 (R2), respectively, with repetitive amino acid sequences rich in proline Gly-Gly-X-X-Pro (GGXXP) (SEQ. ID. No. 7) and Pro-Gln-Pro (PQP) motifs. The R1 region is located in the protruding loop proximal to the aminoterminal sequence (N-terminal) and near to the RGD motif, while the R2 region is located near to the carboxyl terminal end (C-terminal) [Hijnen, M., et al. Infect Immun, 2004. 72(7): p. 3716-23]. Up to 12 different variants of Prn (Prn1, Prn2, Prn3 . . . Prn12) have been identified in *B. pertussis*, as shown in the database of the National Center for Biotechnology Information of the United States of America (NCBI). Strains bearing the Prn1, Prn2 and Prn3 are distributed worldwide. Numerous strain characterization studies, either retrospective or of strains currently circulating, were carried out in American, European, Asian and Australian regions and showed a tendency towards a progressive persistence of Prn2 strains over Prn1 strains, the Prn2 strains predominating in most of the countries studied [Mooi, F. R., et al. Infect Immun, 1998. 66(2): p. 670-5; Cassiday, P et al. J Infect Dis, 2000. 182(5): p. 1402-8; Weber, C. et al. J Clin Microbiol, 2001. 39(12): p. 4396-403; Hallander, H. O., et al. J Clin Microbiol, 2005. 43(6): p. 2856-65; van Amersfoorth, S. C., et al. J Clin Microbiol, 2005. 43(6): p. 2837-43; Byrne, S, et al. BMC Infect Dis, 2006. 6: p. 53].

Current differences in the amino acid sequence of Prn between cellular (DPTc) or acellular (DPTa) vaccines and circulating strains is one of the factors supporting the hypothesis of the efficacy loss of vaccines available, due to the appearance of new strains. Studies in populations vaccinated with DPTc or (DPTa), and non-vaccinated populations, in Netherlands and Italy indicated that these types of vaccines protect better against circulating strains similar to the vaccine strain [Mooi, F. R., et al. Infect Immun, 1998. 66(2): p. 670-5; Mastrantonio, P., et al. Microbiology, 1999. 145 (Pt 8): p. 2069-75]. In agreement with these findings, it was shown in the mice model that vaccination with DPTc differentially protects against strains bearing Prn1 and Prn2, indicating that changes in the Prn R1 region can confer resistance levels [King, A. J., et al. Microbiology, 2001. 147(Pt 11): p. 2885-95]. However, massive studies stratifying *B. pertussis* strains according to country of origin, vaccination status, and type of vaccines (DPTc and DPTa), did not show significant differences in the frequencies of prn, ptxC, ptxA or tcfA2 alleles for circulating strains and vaccination programs [van Amersfoorth, S. C., et al. J Clin Microbiol, 2005. 43(6): p. 2837-43].

The high prevalence of Prn2 strains in many countries is indicative of the favored transmission of these strains by means still unraveled, although the findings mentioned above hardly link the origin of new variants to vaccination. Remarkably, in the above mentioned study [van Amersfoorth, S. C., et al. J Clin Microbiol, 2005. 43(6): p. 2837-43], the three clinically isolated strains bearing allelles similar to that of the vaccines used were found only in non-vaccinated children. Either casual or not, it suggests that Prn1 strains are favored in niches devoid of specific immunity. On the other hand, the recent identification of a phage infecting *Bordetella* (BPP-1) by using Prn as primary receptor, suggested that variations in this protein might be triggered by selective pressures other than those imposed by the immune system [Liu, M., et al. Science, 2002. 295(5562): p. 2091-4]. The possible influences of both phenomena, together with other unknown factors leading to harmonized variations in *B. pertussis*, are not excluded.

The evolution of *Pertussis* epidemiology has been simulated by a mathematical model, integrating the incidence of the disease and the pathogen's transmission independently [Aguas, R., et al. Lancet Infect Dis, 2006. 6(2): p. 112-7]. This model predicts that regular boosting doses would not be capable of eliminating the severity grades of the disease, observed in current epidemics. It is highly probable that this should be caused by the short lifespan of the protection conferred by the available acellular vaccines (4-12 years), and also the variability of the immune response and the different types of vaccines. This model predicts as the most optimistic scenario that where vaccines could generate an immunity superior to the natural one, a paradigm still unreached by the cellular and acellular vaccines available.

The main purpose of the present invention resides on the contribution to develop more efficacious acellular vaccines against Whooping Cough. The main work preceding the present invention were based on administering immunogenic preparations obtained by mixing Prn proteins (Nicole Guiso et al., WO 01/90143 A2 y US 2006/0008474 A1) or synthetic peptides of the Prn R1 region (Frederik Mooi et al., WO 02/00695 A2). Therefore, the development of more efficacious acellular vaccines is an important problem to prevent Whooping Cough.

DETAILED DESCRIPTION OF THE INVENTION

This invention contributes to solve the above mentioned problems, and comprises the engineering of the prnA gene, coding for the outer membrane protein of *B. pertussis* denominated Pertactin (Prn). This invention suffices the needs evidenced in the state of the art, making possible obtaining different variants of engineered Prn, in such a way that they comprise in their structure two different polymorphic domains of the Prn R1 region. The versatility of the invention also covers the engineering of new Prn molecules, additionally comprising three or more different polymorphic domains of the Prn R1 region.

Is subject of the present invention a polynucleotidic sequence coding for an engineered Prn protein, wherein said protein comprises up to the first 300 amino acids proximal to the N-terminal end of a natural, mature Prn of a given type (PrnX300), and an aminoacidic sequence comprising up to 620 amino acids proximal to the C-terminal end of a natural, mature Prn of given type (PrnY620), resulting in an engineered PrnX300-PrnY620Prn protein.

In the context of the present invention, the term 'engineered Prn' refers to a protein resulting from coupling, adjacently or not, of a fragment comprising up to the first 300 amino acids proximal to the N-terminal end of a given natural, mature Prn protein, to another fragment comprising the last 620 amino acids proximal to the C-terminal end of a natural, mature Prn protein.

The new Prn engineered variants are obtained by molecular mutagenesis, by adjacent coupling of sequences comprising up to the first 300 amino acids proximal to the N-terminal end of a natural, mature Prn of a given type, to sequences comprising up to the last 620 amino acids proximal to the C-terminal end of a natural, mature Prn of a given type. The new variants of engineered Prn comprise sequences from the same or different type of Prn in a single molecule, without affecting the protective immune response.

In a preferred embodiment of the present invention, different variants of Prn engineered variants are obtained, encoded by the nucleic acid sequences identified as SEQ ID NO 1-6. Highly significantly protection levels and opsonophagocytic activities were obtained by immunizing mice with the different variants of engineered Prn, higher than those obtained with natural Prn molecules formulated alone or combined in mixes. The immune response generated with the engineered Prn was equally effective against strains expressing different types of Prn.

In a preferred embodiment of the present invention, the fragment comprising the first 300 amino acids proximal to the N-terminal end of a natural, mature Prn of a given type, named PrnX300, corresponds to Prn from the genera *Bordetella*. In another preferred embodiment of the present invention, this fragment corresponds to Prn molecules from *B. pertussis* or *B. parapertussis*, preferably Prn1, Prn2 and Prn3 variants of *B. pertussis*.

In a preferred embodiment of the invention, the las 620 amino acids proximal to the C-terminal end of a natural, mature Prn of a given type, named PrnY620, corresponds to Prn from the genera *Bordetella*. In another preferred embodiment of the present invention, this fragment corresponds to Prn molecules from *B. pertussis* or *B. parapertussis*, preferably Prn1, Prn2 and Prn3 variants of *B. pertussis*.

The polynucleotidic sequence of the present invention codes for a polypeptidic sequence comprising any possible combination of Prn types in the format PrnX300-PrnY620.

The amino acid sequences PrnX300 and PrnY620 coded by the polynucleotide sequence of the present invention are adjacently coupled, or by using the amino acid sequences IDNATWVMTDN (SEQ. ID. No. 8) or IDNATWVMTDNIDNATWVMTDN (SEQ. ID. No. 9).

In the present invention, the amino acid sequences PrnX300 and PrnY620 can be devoid of repetitive sequences, preferably of GGXXP (SEQ. ID. No. 7) and PQP sequences of the R1 and R2 regions. The evidences supporting this design are the following: the Region 1 (R1), comprising the repetitive sequence GGXXP is weakly recognized by human and rabbit sera, indicating that it is not an immunodominant region [Hijnen, M., F. R. Mooi, et al. (2004). Infect Immun 72(7): 3716-23]. On the other hand, recent work reported Prn mutants where the repetitive GGXXP (SEQ. ID. No. 7) and PQP sequences or regions containing these sequences were deleted. GGXXP (SEQ. ID. No. 7) deletions did not affect the physicochemical properties of the mutant Prn molecules obtained, as evidenced in the similar methods used for expression and purification of mutant and non-mutant Prn proteins [Hijnen, M., P. G. van Gageldonk, et al. (2005). Protein Expr Purif 41(1): 106-12]. Similarly, deletions of the GGXXP (SEQ. ID. No. 7) sequences did not significantly affect structural properties, since Prn molecules mutated in R1 were well recognized by MAbs generated against conformational epitopes in natural Prn molecules, and also not recognized by anti-GGXXP MAbs directed against linear GGXXP (SEQ. ID. No. 7) epitopes. Additionally, it was observed that certain mutations inside R1 can enhance the binding capacity to certain MAbs against conformational epitopes. Finally, there were evidences indicating that R1 (GGXXP) (SEQ. ID. No. 7) and R2 (PQP) form a single epitope [Hijnen, M., R. de Voer, et al. (2007). Vaccine 25(31): 5902-14].

In another preferred embodiment of the present invention, the said polynucleotidic sequence codes for an engineered Prn, wherein said amino acid PrnX300 and PrnY620 sequences comprise heterologous peptides able to function as T helper cell epitopes isolated from Diphtheria, Tetanus, the hepatitis B virus (HBV), Polioviruses, Vaccinia, the human immunodeficiency virus (HIV) or the human Influenza virus. It is well known among people skilled in the art that the immune response against a given antigen can be enhanced by including this type of epitopes.

An additional preferred embodiment of the present invention comprises the polynucleotidic sequences according to claim 1, wherein said polynucleotide sequences could be optimized for optimal codon usage, to increase the expression of the encoded protein in bacteria, yeast, insect or mammalian cells. The resulting increase in the expression of the molecules encoded by recombinant procedures is widely know by people skilled in the art in this particular technical field.

In another preferred embodiment, the new protein subject of the present invention can be one of the multiple components of a new combined vaccine, emphasizing that none of the precedent inventions comprised obtaining the minimal number of molecular entities satisfying the existing requirements of this technical field.

Finally, the demands for vaccine preparations able to generate cross-protection between *B. pertussis* and *B. parapertussis* are more than evident in the state of the art. The present invention also comprises generating engineered Prn molecules comprising in a single structure different polymorphic regions of different *Bordetella* species, based on the high homology levels existing between Prn proteins of the different *Bordetella* species.

Unexpectedly, the engineered Prn subject of the present invention was not only capable of inducing an effective immune response against different Prn1- and Prn2-expressing *B. pertussis* strains, but also generated antibody responses more effective than that generated by other non-engineered recombinant Prn proteins, as evidenced in the mice respiratory challenge model and the opsonophagocytic assay. Surprisingly, the immune response induced by the engineered Prn was superior to that induced by an equimolar mix of Prn1 and Prn2 (Prn1+Prn2).

Vaccine compositions made by mixing different Prn proteins of the same or different species, although covering polymorphisms, lead to technical difficulties associated to the new production processes, such as the undesired increase in the concentration of contaminants and the productive inconsistency between lots. This is an essential aspect to develop combined vaccines, composed of multiple antigens with quite different characteristics, which can compromise the systemic immunogenicity of the formulation. On the other hand, it is expected that strategies based on synthetic peptides of the R1 region could lead to vaccines less effective than vaccines currently available, by excluding other epitopes present in the natural Prn from the antigen, relevant to develop a protective response.

To meet this unsolved requirement of this technical field, the present invention comprises a pharmaceutical composition comprising one or more engineered Prn, coded by polynucleotidic sequences from Claims 1 to 13, in amounts sufficient to generate humoral and cellular immune responses effective against *Bordetella* species, when administered through immunization procedures in mammals, and preferably, in humans. In a preferred embodiment of the present invention, the pharmaceutical composition comprising one or more Prn engineered variants generates humoral and cellular immune responses effective against *B. pertussis*.

It is also the aim of the present invention a life or attenuated vaccine comprising one or more Prn engineered variants, coded by sequences from Claims 1 to 13, wherein said Prn engineered variants are expressed in the outer membrane of the life or attenuated organism. In this live or attenuated vaccine, said polynucleotidic sequences from Claims 1 to 13 are included in a plasmid vector or a bacterial chromosome.

In another embodiment of the present invention, said polynucleotidic sequences from Claims 1 to 13, which code for Prn engineered variants, are included in a vector for expression in mammalian cells. In another embodiment of the present invention, said expression vector which contains the polynucleotidic sequences from Claims 1 to 13 is the basis for a nucleic acids vaccine.

In another embodiment of the invention, the polypeptidic sequences coded by said polynucleotidic sequences from Claims 1 to 13, can be used to detect *Bordetella* infections. Is also the aim of the present invention a diagnostic kit to detect the presence or absence of antibodies against *Bordetella*, comprising polypeptidic sequences coded by the polynucleotidic sequences referred on Claims 1 to 13.

DETAILED DESCRIPTION OF THE EMBODIMENTS/EXAMPLES

Example 1

Figure 1:
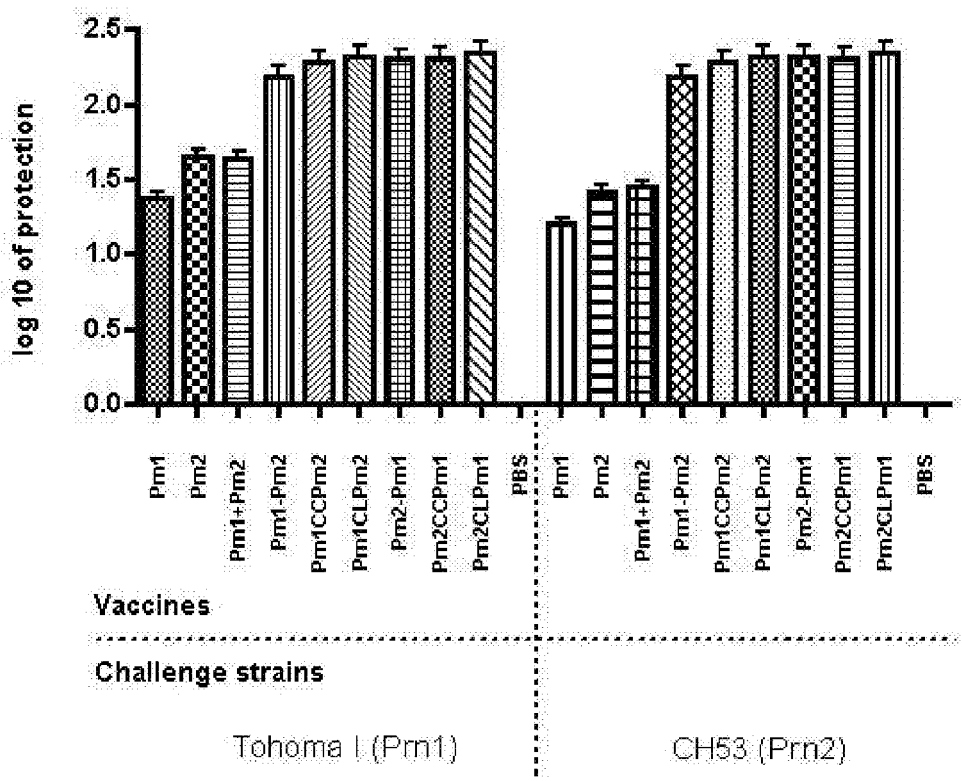
FIG. 1. Protection experiment in Balb/c mice vaccinated with different recombinant Prn engineered variants. Strains of *B. pertussis* Tohama I (Prn1) and the clinical isolate CH53 (Prn2) were used as challenge. Barrs represent the mean logarithm of the reduction of viable bacterial cells in lungs.
Figure 2:
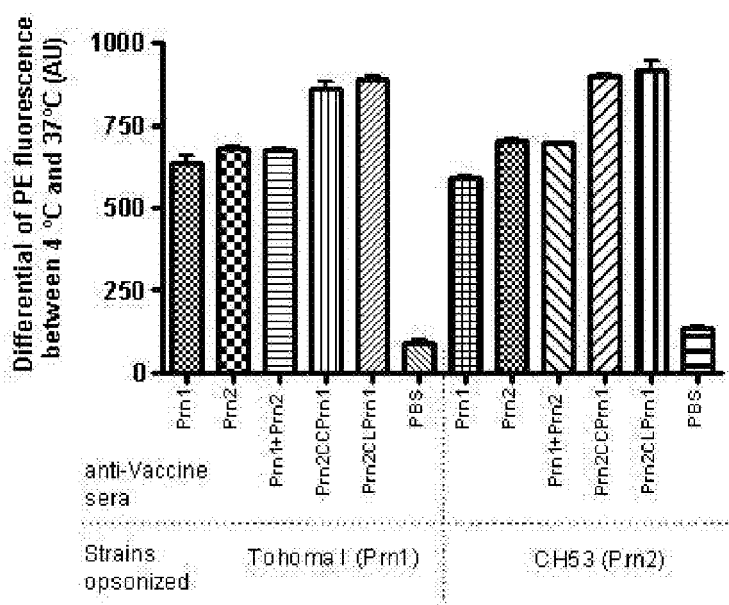
FIG. 2. Opsonophagocytosis mediated by sera from Balb/c mice vaccinated with the different recombinant Prn engineered variants. The chart shows the difference of fluorescence (phycoerythrin, PE) in arbitrary units (AU) of cells stained with fluorescein isothiocyanate (FITC) in two incubation conditions (PE 4° C.-PE 37° C.).
Figure 3:
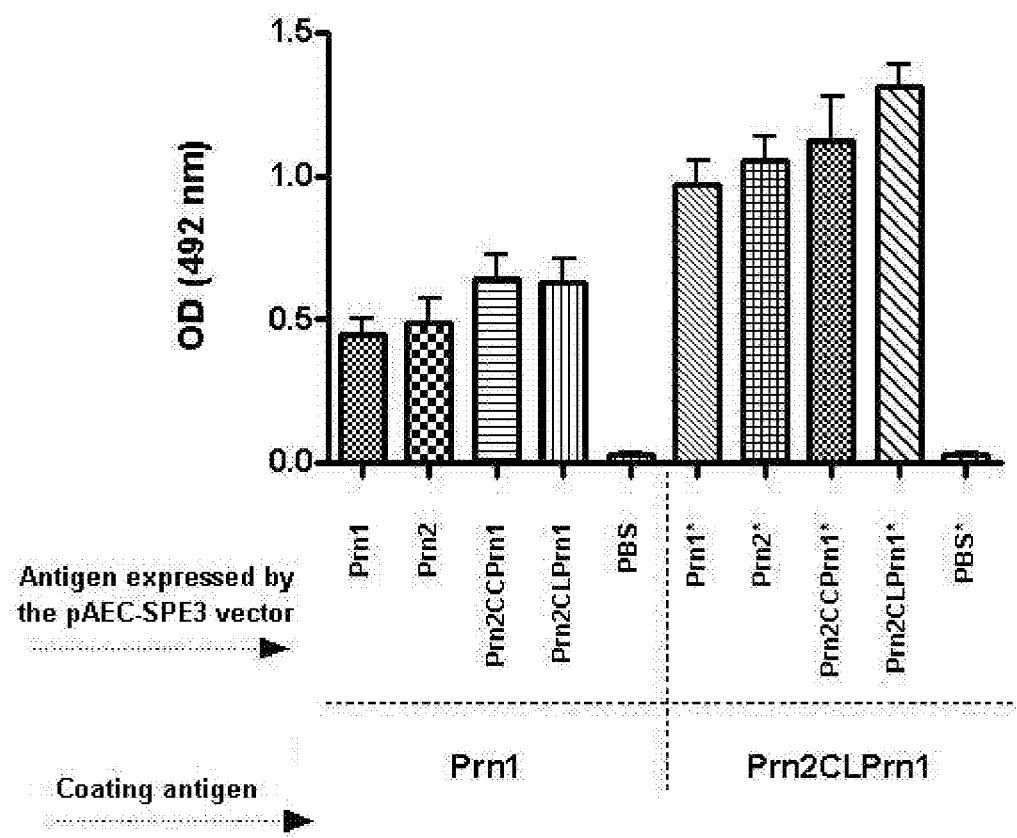
FIG. 3. Humoral IgG immune response against Prn1 and Prn2CCPrn1 generated in mice immunized with plasmids expressing the Prn1, Prn2, Prn2CCPrn1 and Prn2CLPrn1 engineered variants.

Construction of Vectors for the Intracellular Expression in *Escherichia coli* of the Different Prn Engineered Variants and its Purification The prnA1 and prnA2 genes from *Bordetella* strains *B. pertussis* Tohoma I (Prn1) and CH53 (Prn2) were amplified by Polymerase Chain Reaction (PCR) from genomic DNA by using the previously reported oligonucleotides 1 and 2 [Hijnen, M., P. G. van Gageldonk, et al. (2005). Protein Expr Purif 41(1): 106-12].

The fragments obtained were cloned into the vector pET-28$^a$ (Novagen) using the sites Nde I and BamH I. The Prn engineered variants were obtained by using the reverse PCR method previously reported by Imai and co-workers in 1991 [Imai, Y., et al. Nucleic Acids Res, 1991. 19(10): p. 2785]. Nucleotides used to amplify the different polynucleotidic sequences are shown in Table 1. The oligonucleotide pair 1,2 was used to linearize vector pET28aprn1 and pETaprn2, corresponding to Prn1 and Prn2, respectively. The DomR1 fragments were obtained by amplification with oligonucleotides 3 and 4. Additionally, this region was amplified by using the nucleotide pairs 3,5 and 3,6 to add sequences coding for the short and long linkers, respectively. The conditions used for PCR amplification of the fragments used in the present invention are summarized in Table 2.

TABLE 1

Oligonucleotides used for amplification of the different sequences.

| Number | Oligonucleotide name | Sequence 5'→3' | Result of the PCR amplification |
|---|---|---|---|
| 1 | pET28aprn1 1401-1430 LinVect | AGCGTGGAGCTCGCCCA GTCGATCGTCGAG (SEQ ID NO. 10) | Linearized vector with blunt ends |
| 2 | pET28aprn1 1431-1460 LinVect | GGAGCCCGATACGTCCA CGCCATACCAGCC (SEQ ID NO. 11) | |
| 3 | pET28aprn1 1975-1997 DomR1 | GTCAAGGCCGGCAAGCT GGTCGC (SEQ ID NO. (SEQ ID NO. 12) | Domain R1 (DomR1) of any type of Prn |
| 4 | pET28aprn1 1431-1453 DomR1 | GGAGCCCGATACGTCCA CGCCAT (SEQ ID NO. 13) | |
| 5 | pET28aprn1 1431-1453 DomR1 CC-Nt | ATCGACAACGCCACCTG GGTCATGACGGACAACG TCAAGGCCGGCAAGCTG GTCGC (SEQ ID NO. 14) | Amplifies DomR1 from any type of Prn, also adding a linker of 11 amino acids to the N-term. |
| 6 | pET28aprn1 1431-1453 DomR1 CL-Nt | ATCGACAACGCCACCTG GGTCATGACGGACAACA TCGACAACGCCACCTGG GTCATGACGGACAACGT CAAGGCCGGCAAGCTG (SEQ ID NO. 15) | Amplifies DomR1 from any type of Prn, also adding a linker of 22 amino acids to the N-term. |

TABLE 2

Conditions for PCR amplification of the different fragments used in the present invention

| Oligonucl pair | Hybridation temp (° C.). | Template DNA (µg) | Extension time (min) | Polymerase (Units) | No. of cycles | Amplific. product | Size of the amplific. product (bp) |
|---|---|---|---|---|---|---|---|
| 1, 2 | 65 | pET28aprn1 (1) | 7.5 | Pfx (2.5) | 5 | Vector Lineal | 7370 |
| 1, 2 | 65 | pET28aprn2 (1) | 7.5 | Pfx (2.5) | 5 | Vector Lineal | 7385 |
| 3, 4* | 67 | pET28aprn1 (0.1) | 0.6 | Pfu (2.5) | 30 | DomR1 prn1 | 567 |
| 3, 4* | 67 | pET28aprn2 (0.1) | 0.6 | Pfu (2.5) | 30 | DomR1 prn2 | 582 |
| 3, 5* | 67 | DomR1 prn1 (0.1) | 0.6 | Pfu (2.5) | 30 | CC-DomR1 prn1 | 600 |
| 3, 6* | 67 | DomR1 prn1 (0.1) | 0.6 | Pfu (2.5) | 30 | CL-DomR1 prn1 | 633 |
| 3, 5* | 67 | DomR1 prn2 (0.1) | 0.6 | Pfu (2.5) | 30 | CC-DomR1 prn2 | 620 |
| 3, 6* | 67 | DomR1 prn2 (0.1) | 0.6 | Pfu (2.5) | 30 | CL-DomR1 prn2 | 648 |

*Phosphorylated oligonucleotides,
CC: Short linker,
CL: Long linker

The linearized pET28aprn1 and pET28aprn2 vectors, obtained by reverse PCR, were ligated to the different fragments coding for domains containing region 1 from Prn1 and Prn2. In these vectors, the new engineered genes are under the transcriptional control of the T7 inducible promoter. Clones bearing the correct sequences were introduced into the BL21-Codonplus(DE3)-RP *E. coli* strain, for the expression of the corresponding proteins as inclusion bodies [Hijnen, M., et al. Protein Expr Purif, 2005. 41(1): p. 106-12].

The expression levels of the recombinant Prn1 and Prn2, as well as for the other variants, reached between 15 and 20% of total proteins, as evidenced by densitometry in polyacrylamide gels stained with Coomassie blue.

The different proteins were purified by suspending the bacterial paste for each variant in rupture buffer (at a cell concentration of 100 mg/mL) and cells were lysed with ultrasound. The cellular pellets were solubilized in 8 M Urea and fractionated by Sodium Dodecyl Sulphate polyacrylamide gel electrophoresis (SDS-PAGE, 12.5%). The gel was stained by reverse Zinc-Imidazol staining, and the slice containing the band corresponding to the protein of interest was passed through a stainless steel mesh of 100 µm in the presence of extraction buffer. The protein was further extracted, and renatured and concentrated by ultrafiltration through an Amicon concentration cell, with a membrane of 50 kDa, and the final concentration was determined by the Bicinchoninic acid method. No contaminants were detected by assaying 15 μg of each protein purified from the analytical SDS-PAGE gels stained with Coomassie blue, evidencing that protein preparations were more than 95% pure. The characteristics of the different constructs and the Prn engineered variants obtained are summarized in Table 3.

TABLE 3

Characteristics of the different Prn constructs and Prn engineered variants

| Plasmid name | Linker between DomR1 | Name of the engineered Prn | Prn type | Characteristics of the engineered Prn |
|---|---|---|---|---|
| pET28aprn1 | No | Prn1 | 1 | — |
| pET28aprn2 | No | Prn2 | 2 | — |
| pETprn DomR1 (1-2) | No | Prn1-Prn2 | 1, 2 | Nt . . . DomR1 (Prn1)-DomR1(Prn2) . . . Ct |
| pETprn DomR1 (1-CC-2) | IDNATWVMTDN | Prn1-CC-Prn2 | 1, 2 | Nt . . . DomR1 (Prn1)-CC-DomR1(Prn2) . . . Ct |
| pETprn DomR1 (1-CL-2) | IDNATWVMTDNIDNATWVMTDN | Prn1-CL-Prn2 | 1, 2 | Nt . . . DomR1 (Prn1)-CL-DomR1(Prn2) . . . Ct |
| pETprn DomR1 (2-1) | — | Prn2-Prn1 | 1, 2 | Nt . . . DomR1 (Prn2)-DomR1(Prn1) . . . Ct |
| pETprn DomR1 (2-CC-1) | IDNATWVMTDN | Prn2-CC-Prn1 | 1, 2 | Nt . . . DomR1 (Prn2)-CC-DomR1(Prn1) . . . Ct |
| pETprn DomR1 (2-CL-1) | IDNATWVMTDNIDNATWVMTDN | Prn2-CL-Prn1 | 1, 2 | Nt . . . DomR1 (Prn2)-CL-DomR1(Prn1) . . . Ct |

Example 2

Active Immunization, Antibody Response and Protection in a Mice Model

Mice were immunized with 0.2 μg or 0.02 μg of the recombinant Prn1 and Prn2, PBS, an equimolar mix of Prn1 and Prn2 (Prn1+Prn2), and six of the Prn engineered variants (shown in Table 3). All the proteins were administered formulated in alum. Doses corresponded to 1/40 and 1/400 fractions of the dose commonly employed in humans (Infanrix®, 8 μg). Mice were immunized by the subcutaneous route, with a volume of 100 μL. Sera from the immunized mice were evaluated by an ELISA type immunoenzymatic assay. The antibody titers reached mean values from $1.2 \times 10^3$ to $4.6 \times 10^4$. The mean values of the titers for corresponding to the highest doses significantly differed from the titers reached with the lowest doses used, for all the cases ($p<0.05$, Kruskal Wallis-Dunns). No differences were observed in the antibody response generated with Prn1, Prn2 or the equimolar mix Prn1+Prn2. Similarly, there were no differences between the mean titers of the different Prn engineered variants. Surprisingly, the titers obtained with the Prn engineered variants were significantly higher than those generated by the non-engineered recombinant Prn proteins ($p<0.01$, Kruskal Wallis-Dunns).

The strain Tohama I (Prn1) and the clinical isolate CH53 (Prn2) were used for the intranasal challenge. Bacteria were cultures in plates containing Bordet-Gengou-Agar media (Sigma) supplemented with 1% glycerol and 14% defibrinated goat blood. Plates were incubated for 24 h at 37° C. and the resulting colonies were suspended in Stainer-Scholte medium at a $10^8$ cells/mL concentration. This suspension was used for the intranasal challenge. Mice immunized were challenged 15 days after the last immunization, by instillation of 50 μL of the bacterial suspension ($5 \times 10^6$ cells). Five days after challenge, mice were sacrificed and lungs aseptically extracted and homogenized to measure the bacterial burden [Denoel, P., et al. Vaccine, 2005. 23(46-47): p. 5333-41]. The different variants showed protection levels significantly higher than the non-vaccinated controls ($p<0.001$). Unexpectedly, the engineered Prn variants showed higher protection levels when compared with the recombinant Prn proteins or the equimolar Prn1+Prn2 mix for both strains ($p<0.001$).

The Prn engineered variants showed similar protection levels against both strains at the lowest administered dose, an effect unattained with the Prn1 or Prn2 proteins. These results evidence that these Prn engineered variants bear immunological properties different from, and superior to, those showed by the recombinant Prn1 and Prn2 proteins assayed both separately or as equimolar mixes (FIG. 1).

Example 3

Opsonophagocytic Activity in Sera

The opsonophagocytic activity mediated by anti-Prn sera has been shown as a crucial parameter in the response of people vaccinated with acellular vaccines [Hellwig, S. M., et al. J Infect Dis, 2003. 188(5): p. 738-42]. The present invention shows that the different Prn engineered variants were capable of inducing antibodies resembling these properties. The opsonophagocytic activity was studied by the previously mentioned method, adapted to the mice model. Strains Tohama I and CH53 of *B. pertussis* were grown in Bordet-Gengou-Agar and the cells stained with FITC ($2\times10^6$ colony-forming units). Afterwards, the labeled bacteria were opsonized for 30 min at 37° C., in a plate shaker, with sera from mice immunized with the recombinant Prn1, Prn2, Prn1+Prn2 and two variants of the engineered Prn proteins (Prn2-CC-Prn1 and Prn2-CL-Prn1). During the adhesion step, the opsonized bacteria and the non-opsonized control were incubated with polymorphonuclear cells (PMN). Samples were further divided into two equal subgroups of cells, one incubated for another 45 min at 4° C. and the other at 37° C. All the samples were finally incubated for another 30 min at 4° C. with the goat anti-mouse-PE labeled conjugate. Samples were analyzed by flow cytometry (PARTEC PAS III). The fluorescence intensities of green- and red-stained cells incubated at 4° C. were used as adhesion controls. The difference of red fluorescence in green-stained cells was used to evidence the phagocytic activity mediated by sera.

The Prn engineered variants showed opsonophagocytic activity (FIG. 2). Surprisingly, there were significant differences only in among the groups immunized with the Prn engineered variants when compared with mice inoculated with PBS ($p<0.05$, Kruskal Wallis-Dunns). The opsonophagocytic activity of sera generated by the recombinant, non-engineered Prn protein alone or in combination reached values 6-fold higher than the PBS control, although these differences were not significant. Finally, these results evidenced that the Prn engineered variants are able to induce antibodies with significant opsonophagocytic activity, irrespective of the type of Prn present in the bacterium.

Example 4

Construction of Vectors for the Expression in Mammals of Prn Engineered Variants and Evaluation of the Humoral Immune Response Generated The genes prnA1 and prnA2, and the gene variants prn2CCprn1 and prn2CLprn1, were amplified by PCR from their respective expression vectors (see Table 3) by using the previously reported oligonucleotides 1 and 2 [Hijnen, M., P. G. van Gageldonk, et al. (2005). Protein Expr Purif 41(1): 106-12]. In this case, the oligonucleotide 1 was modified, substituting the Nde I by a BamH I restriction site. The fragments obtained were cloned into the BamH I restriction site of the pAEC-SPE3 plasmid vector [Herrera A M, Rodriguez E G, et al. (2000) BBRC, 279, 548-551]. This vector is designed for the extracellular expression of antigens in mammalian cells. The resulting constructs were purified by using the commercial plasmid DNA purification kit Endo-free plasmid Giga kit (Qiagen). Groups of female 6-to-7-week-old Balb/c mice were immunized thrice with 100 μg of DNA in 100 μL of PBS, at three-week intervals by the intraperitoneal route. The control group was immunized with the empty vector without insert (pAEC-SPE3). Fifteen days after the last immunization, mice were sacrificed and blood collected for the evaluation of sera. The specific IgG antibody responses were evaluated by the ELISA technique, at a 1/1000 dilution and coating plates with equimolar amounts of the Prn1 (2 μg/mL) and Prn2CCPrn1 (2.4 μg/mL) proteins. As shown in FIG. 3, animals immunized with the different plasmids expressing Prn1, Prn2, Prn2CCPrn1 and Prn2CLPrn1 generated specific IgG antibody responses, significantly higher ($p<0.001$) than animals immunized with the empty pAEC-SPE3 vector. Similarly to sera generated in mice immunized with protein and alum (data not shown), sera from immunized mice preferentially recognized the Prn engineered variant Prn2CCPrn1 ($p<0.05$), more than the natural Prn1 protein, what could be due to a better exposure of the shared epitopes in Prn2CCPrn1 than in Prn1.

The invention claimed is:

1. An isolated polynucleotide sequence coding for a pertactin (Prn) engineered protein, wherein said isolated polynucleotide sequence codes for up to the first 300 amino acids proximal to the N-terminal end of a given type of natural, mature Prn (PrnX300) and an amino acid sequence comprising up to the last 620 amino acids proximal to the C-terminal end of a given type of natural, mature Prn (PrnY620), resulting in an engineered PrnX300-PrnY620 pertactin, and wherein the polynucleotide sequence comprises SEQ. ID. NO: 3.

2. The isolated polynucleotide sequence according to claim 1, wherein said PrnX300 amino acid sequence comprises Prn sequences from the *Bordetella* genera.

3. The isolated polynucleotide sequence according to claim 2, wherein said PrnX300 amino acid sequence comprises Prn sequences from *B. pertussis* or *B. parapertussis*.

4. The isolated polynucleotide sequence according to claim 3, wherein said PrnX300 amino acid sequence comprises Prn sequences from Prn1, Prn2 and Prn3 of *B. pertussis*.

5. The isolated polynucleotide sequence according to claim 1, wherein said PrnY620 amino acid sequence comprises Prn sequences from the *Bordetella* genera.

6. The isolated polynucleotide sequence according to claim 5, wherein said PrnY620 amino acid sequence comprises Prn sequences from *B. pertussis* or *B. parapertussis*.

7. The isolated polynucleotide sequence according to claim 3, wherein said PrnY620 amino acid sequence comprises Prn sequences from Prn1, Prn2 and Prn3 of *B. pertussis*.

8. The isolated polynucleotide sequence according to claim 1, wherein said polynucleotide sequence codes for a polypeptide comprising any possible combination of Prn of any type in the format PrnX300-PrnY620.

9. The isolated polynucleotide sequence according to claim 1, wherein said PrnX300 and PrnY620 amino acid sequences are coupled adjacently, or by means of IDNATWVMTDN (SEQ. ID. No. 8) or IDNATWVMTDNIDNATWVMTDN (SEQ. ID. No. 9) amino acid sequences.

10. The isolated polynucleotide sequence according to claim 1, wherein said PrnX300 and PrnY620 amino acid sequences are devoid of repetitive sequences, and more precisely, devoid of GGXXP (SEQ. ID. No. 7) and PQP repetitive sequences from Prn regions R1 and R2.

11. The isolated polynucleotide sequence according to claim 1, wherein said PrnX300 and PrnY620 amino acid sequences additionally comprise peptides with T helper epitopes.

12. The isolated polynucleotide sequence according to claim 11, wherein said peptides are obtained from Diphtheria, Tetanus, HBV, Poliovirus, Vaccinia, HIV or Influenza virus.

13. The isolated polynucleotide sequence according to claim 1, that has an optimized codon usage for optimal expression in bacteria, yeast, insect or mammalian cells.

14. A pharmaceutical composition comprising a polynucleotide sequence according to claim 1.

15. A pharmaceutical composition according to claim 14, wherein said pharmaceutical composition generates effective humoral and cellular immune responses against *B. pertussis*.

16. An isolated expression vector comprising isolated polynucleotide sequence according to claim 1, wherein said sequence codes for engineered Prn molecules.

17. A method to detect *B. pertussis* or *B. parapertussis* infections comprising the use of a polynucleotide sequence according to claim 1.

18. A diagnostic kit for detection of *B. pertussis* or *B. parapertussis*, wherein said diagnostic kit comprises a polynucleotide sequence according to claim 1.

* * * * *